United States Patent [19]

King, III et al.

[11] Patent Number: 4,675,424
[45] Date of Patent: Jun. 23, 1987

[54] METHOD FOR MAKING POLYSILAZANES

[75] Inventors: Roswell E. King, III, Pleasantville; Bernard Kanner, West Nyack; Steven P. Hopper, Carmel; Curtis L. Schilling, Jr., Croton-on-Hudson, all of N.Y.

[73] Assignee: Union Carbide Corporation, Danbury, Conn.

[21] Appl. No.: 841,545

[22] Filed: Mar. 19, 1986

[51] Int. Cl.$^4$ .............................................. C07F 7/10
[52] U.S. Cl. .................................... 556/412; 556/410; 501/97; 501/154; 528/28; 528/38; 423/344
[58] Field of Search .................. 556/410, 412; 501/97, 501/154; 423/344; 528/28, 38

[56] References Cited

U.S. PATENT DOCUMENTS

| | | | |
|---|---|---|---|
| 4,404,153 | 9/1983 | Gaul | 556/410 X |
| 4,482,669 | 11/1984 | Seyforth et al. | 556/412 X |
| 4,482,689 | 11/1984 | Haluska | 556/412 X |
| 4,540,803 | 9/1985 | Cannady | 556/412 |

Primary Examiner—Paul F. Shaver
Attorney, Agent, or Firm—P. W. Luezzi

[57] ABSTRACT

A method of preparing silazane polymers, with 3 or more repeating units, of the general formula

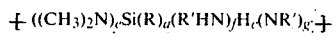

and a $(CH_3)_2NH$ byproduct group where R is hydrogen, an alkyl group having 1-6 carbon atoms or an aryl group having 6-12 carbon atoms, a=0, or 1, b=2-4, C=0-2, d=0 or 1, e=0-2, f=0-2, g=1-3 and a+c+e+f+g=4 for the polymer units; and R' is hydrogen or methyl, whereby the silazane polymer is substantially free of halide impurities, and wherein this method comprises:

transaminating an aminosilane of the general formula $(R)_a((CH_3)_2N)_bH_cS$; where R is defined as above and a+b+c=4 with an amine of the general formula $(CH_3)_dNH_{3-d}$ whereby d is defined as above and the amine has a molecular weight lower than 45 all in the presence of an acid catalyst or the ammonium salt of the acid and thereafter condensing to form the polymer.

37 Claims, No Drawings

METHOD FOR MAKING POLYSILAZANES

BACKGROUND OF THE INVENTION

1. Field of The Invention

This invention generally relates to a novel process for making polysilazanes substantially free of halide impurities. More particularly, this invention relates to a liquid phase process for making polysilazanes via the transamination and condensation of certain aminosilanes, particularly tris-dimethylaminosilane and/or vinyl-tris (dimethylamino)silane, with ammonia and/or monomethylamine in the presence of a Bronsted acid catalyst. The resulting polysilazane polymers range from fluids and resins to insoluble powders. These silazane polymers can be used as precursors for silicon based ceramic materials, binders or fibers.

2. Prior Art

Silicon nitride, $Si_3N_4$, is currently a material of great potential and interest in that its ceramic properties include high temperature stability, chemical inertness, oxidation resistance and extreme hardness. In the past, silicon nitride has been prepared by a variety of methods, including the reaction of silicon metal with gaseous N2 and/or $NH_3$, giving reaction-bonded silicon nitride, ("RSBN"). RSBN is useful for forming bulk parts via methods of powder metallurgy; for example hot pressing, sintering, casting or extruding.

Another method of preparing silicon nitride is via chemical vapor deposition ("CVD"). The reaction of $H_{4-x}SiCl_x$, where x=0, 1, 2, 3 or 4, with $NH_3$ in the gas phase at high temperatures results in the preparation of high purity silicon nitride. The purity of the product is related to the purity of the reactant gases. The CVD method is a fundamental process for fabricating electronic materials and devices which require high purity silicon nitride.

Recently, routes have been developed for making silicon containing ceramics from the pyrolysis of polyorganosilazanes, such as described in U.S. Pat. No. 3,853,567 to Verbeek et al. and U.S. Pat. No. 3,892,583 to Winter et al.

Typically, these silazane polymers are synthesized from the reaction of halogen containing silanes with ammonia [J. Am. Ceramic. Soc. 67 132 (1984)], or by the reaction of halogen containing alkylsilanes with ammonia [J. Poly. Sci. A2 3179–3189 (1964)], primary amines [Acta. Chem. Scand. 13 29–34 (1959)], diamines [J. Poly. Sci. A2 44–55 (1964)] or silazanes. Because the starting reactant is a halogen containing silane or halogen containing alkylsilane, this amination step results in the synthesis of an amine hydrohalogen byproduct in addition to the desired organosilazane. Two representative reactions are shown below:

Recent U.S. Pat. Nos. 4,535,007, 4,540,803 and 4,543,344 to Cannady teach methods for preparing silicon nitride-containing ceramics by high temperature firing of a $R_3SiNH$ containing silazane polymer. Cannady makes clear that in these patents the $R_3SiNH$-containing hydrosilazane polymers are derived from halogen containing silane or halogen containing alkylsilane reactants.

The prior art also teaches that lower boiling amines, i.e. $NH_3$, can be used to transaminate the dimethylamino groups on $(CH_3)_3SiN(CH_3)_2$ to give trimethylsilylamine, $(CH_3)_3SiNH_2$, which ultimately decomposes at room temperature to give hexamethyldisilazane, $((CH_3)_3Si)_2NH$, Wiberg and Uhlenbrock, Chem. Ber. 104 pp. 2643–2645 (1971). This work however does not teach the production of silazane polymers and does not use acid catalysis.

Consequently, except when silane, $SiH_4$, is used as a starting reactant, there is no teaching in the prior art for making polysilazane polymers free of ammonium hydrogen halide containing byproducts. The use of silane, however, is inherently dangerous due to the explosive reactivity of $SiH_4$ and $O_2$. In addition, those processes in the prior art involving the use of halogen containing silanes to prepare polysilazanes require an imperfect and time-consuming filtration and/or calcination step to substantially eliminate the viscous ammonium hydrogen halide byproducts created by the reaction. These processes thus require a lengthy and difficult filtration process step and/or a time consuming and energy intensive calcination process step. Moreover, these process steps are not always completely satisfactory because of the difficulties inherent in attempting to separate amine hydrohalogen byproducts from the liquid or solid silazane polymer products. Thus, there is a need in the art for a safer, more economic, more expedient and less energy intensive process for making silazane polymers substantially free of halide impurities.

OBJECTIVES

It is thus an object of this invention to provide a more economic, safer and less wasteful process for making polysilazanes substantially free of halide impurities.

It is a further object of this invention to provide such process eliminating the calcination or filtration step needed to remove halide impurities.

Another object of the invention is to provide aminosilanes which can be transaminated by lower weight amines and thus help provide silazane polymers which generate greater weight percent yield of the silicon nitride-containing ceramics upon high temperature pyrolysis of the polysilazanes.

It is yet another object of the invention to provide the ability to use acid catalysts which are sources of carbon dioxide with certain aspects of the invention, i.e., when the starting aminosilane reactant has an —SiH linkage.

Still another object of the invention is to allow the transamination byproduct, e.g., dimethylamine, to be recycled into the process for preparing dimethylaminosilanes.

It is an even further object of the invention to provide a method for preparing new silazane polymer compositions which can be converted by high temperature firing to silicon nitride and silicon nitride containing ceramic materials.

Yet another object of this invention is to provide silazane polymers made by the process of the invention.

Other objects and advantages of the invention will become apparent as the description thereof proceeds.

BRIEF SUMMARY OF THE INVENTION

In satisfaction of the foregoing objects, this invention relates to a novel process for making polysilazanes which can be used as precursors for silicon nitride containing ceramic powders, composites, binders and fibers. This process is economically attractive in that it eliminates a process step for removing halide impurities found in the production of prior art polysilazanes. More specifically, this invention provides the transamination and condensation of certain aminosilanes with ammonia or other useful amines to form hydrosilazane and silazane polymers free of halogen impurities.

The invention provides tris(dimethylamino) silane and certain byproducts and derivatives as starting materials which can be transaminated with ammonia or other useful amines and condensed entirely in one liquid phase and in one vessel to provide polysilazane products. Because these starting aminosilanes are halogen free, substantially no hydrohalogen impurities result. Thus, the difficult and often imperfect solid/solid or liquid/solid phase separation step in which these impurities are filtered or calcined out of the silazane polymer is eliminated.

DETAILED DESCRIPTION OF THE INVENTION

In accordance with the present invention, there is provided a novel process for making polysilazanes from various aminosilanes transaminating amines, acid catalysts, and optionally solvents in a liquid phase reaction.

The general reaction in this method of producing polysilazanes substantially free of halide impurities is a transamination reaction as shown below:

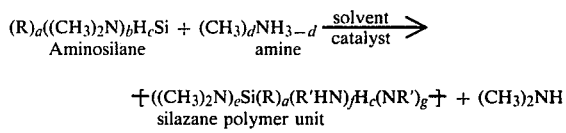

wherein R is hydrogen, an alkyl group having 1–6 carbon atoms or an aryl group having 6–2 carbon atoms, e.g., methyl, ethyl, vinyl, etc., $a=0$ or 1, $b=2-4$, $c=0-2$, $d=0$ or 1, $e=0-2$, $f=0-2$, $g=1-3$ and $a+b+c=4$ for the aminosilane reactants, and $a+c+e+f+g=4$ and R' is hydrogen or methyl for the silazane polymer units.

The silazane polymer unit is subsequently condensed to form the actual polymer as is well known to those skilled in the art (cite). Additionally, all the silazane polymers have three or more repeating units. It should be noted that the $(CH_3)_2NH$ byproduct generated from the reaction can be recycled to further prepare starting aminosilanes.

The starting aminosilanes used in the present invention are prepared by the direct reaction of dimethylamine with silicon metal as is taught in U.S. Pat. No. 4,255,348 to Herdle and Kanner. By using these halogen-free aminosilanes, the present invention is able to provide polysilazanes essentially free of amine hydrohalogen impurities.

For purposes of the instant invention, the aminosilane starting reactant of the general reaction can be divided into two classes:

Class 1 -aminosilanes bearing Si—H linkages
Class 2 -aminosilanes that do not contain Si—H linkage.

This distinction is made between the two classes because, as discussed below, a wider variety of catalysts are effective in the transamination and condensation of Class 1 compounds.

The members of Class 1 can be any alkylaminosilane such as $Me(Me_2N)_2SiH$ or $Et(Me_2N)_2SiH$ or dihydrodiaminosilanes such as $(Me_2N)_2SiH_2$. The preferred member of Class 1 is tris(dimethylamino)silane. Members of Class 2 are compounds derived from $(Me_2N)_3SiH$ via reactions of the hydrosilyl group. These include compounds such as $(Me_2N)_3SiCH=CHSi(NMe_2)_3$, $CH_3CH_2Si(NMe_2)_3$, $(Me_2N)_4Si$, $CH_2=CHSi(NMe_2)_3$, and the like.

The amines of the present invention, with which the aminosilane is transaminated, include the higher equivalent molecular weight amines such as ethylenediamine, propylamine, allylamine, and aniline. These amines may impart useful properties to the polysilazanes as ceramic precursors in application areas such as fibers, coating and matrices for composites.

Other transaminating amines which can be used include ethylene diamine n-butyl amine, sec-butyl amine, tert-butyl amine, cyclohexyl amine, and n-hexyl amine. The preferred amines of the invention, however, are the low molecular weight amines such as ammonia, and/or methyl amine in terms of obtaining the highest weight percent ceramic yields.

In another aspect of this invention, it has been unexpectedly discovered that the starting aminosilanes of the invention can be efficiently displaced, through Bronsted acid catalysis, with amines of lower molecular weight such as the preferred low molecular weight amines mentioned above. These lower molecular weight amines, specifically ammonia or mono-methyl amine, yield silazane polymers which polymers in turn serve as the preferred precursors for silicon nitride containing ceramic compositions.

The prior art teaches the displacement of lower molecular weight amines by higher molecular weight amines rather than the opposite. This is apparently because of the difficulties involved in displacing a higher molecular weight amine group, which has a higher boiling point with a lower molecular weight amine, which, because of its lower boiling point, normally evaporates first. As noted, it has been advantageously found that with the starting reactants used in this invention, displacement of the higher molecular weight amines with lower molecular weight amines is readily feasible. The lower molecular weight amine groups present in the silazane polymers are advantageous because, having little or no carbon content in the silazane polymer, a greater overall weight percent yield of $Si_3N_4$ following pyrolysis is provided. Carbon-containing substituents are lost during high temperature pyrolysis and correspondingly reduce the weight percent yield of the silicon nitride ceramic; low carbon content polymers thus result in higher yields.

The ratio of starting aminosilane to the transaminating amine is not critical to the practice of the invention. A preferred ratio, however, is from 0.01:1 to 2.0:1 molar amounts of starting aminosilane reactant relative to the transaminating amine reactant.

The acid catalysts used in this reaction depend on whether the starting aminosilane is characterized into Class 1 or Class 2 as defined above. When the silicon substrate contains an Si-H linkage, i.e. Class 1, the transamination and subsequent condensation reactions are unexpectedly catalyzed by sources of carbon dioxide. Withholding theoretical or mechanistic arguments, sources of carbon dioxide such as anhydrous $CO_2$ (gas), carbamate salts of the formula $R_2NH_2{}^+R_2NCO_2{}^-$ or carbamatosilane compounds of the formula $(R_{22})_{3-x}(R_2N)_xSiH$ where $x=1$ or 2 do serve as catalysts in both the transamination and the condensation reactions, yielding polysilazane products. The transamination of Class 1 aminosilane compounds is also effectively catalyzed by relatively mild acidic reagents such as carboxylic acids, e.g., acetic acid. The transamination of Class 1 aminosilanes is most efficiently catalysed by the same strong organic or inorganic acid catalysts as discussed below for Class 2 aminosilane compounds.

The transamination of Class 2 aminosilane compounds is relatively unaffected by the mild organic acids mentioned above or "sources of $CO_2$" type catalysis. These Class 2 aminosilanes which do not contain silicon-bonded hydrogen are more effectively transaminated using strong organic or inorganic acids. These more effective strong acid catalysts are characterized by pKa values relative to water of less than 2.2. Representative strong organic acids are the sulfonic acids, e.g., methane sulfonic acid, para-toluene sulfonic acid, or trifluoromethane sulfonic acid. Trifluoroacetic acid is an example of a relatively strong carboxylic acid. Representative examples of strong inorganic acids include sulfuric acid, nitric acid or phosphoric acid.

For the catalysts which are considered sources of carbon dioxide, the loadings are in the range of 0.5-30 mol percent based on starting aminosilane, preferably 1-10 mol percent. For catalysts which are considered strong organic or inorganic acids and may be used with either Class 1 or Class 2 compounds, the loadings are in the range of 0.01-10 mol percent based on starting aminosilane, preferably 0.1-5 mol percent.

The transamination reactions of the present invention can be conveniently run in the presence of appropriate solvents with the stipulation that the solvents should be largely unreactive with the amlnosilane, the incoming amine and the transamination catalyst of the reaction under typical reaction conditions and should allow for reasonable reaction rates. Typical solvents are alkanes such as heptanes, octanes, or decane and alkylated benzenes such as toluene, xylene or mesitylene. Sufficient solvent is used so that the reaction may adequately take place in a liquid environment. The amount of solvent, however, is not critical to the reaction. The preferred ratio of starting reactant to solvent is from 0.1:1.0 to 10:1, preferably 1:1 by either weight or volume.

After the reaction is completed, the solvent may be removed by heat and vacuum evaporation without a filtration step if the resulting polysilazane is a solvent soluble product, or by filtration if the resulting polysilazane is a solvent insoluble product. This filtration step is straightforward and expedient in the sense that it simply separates the insoluble product from the unreactive solvent. This differs from a filtration to remove by-products, such as ammonium hydrogen halide salts, in that it does not require an additional process step, i.e., solvent removal by evaporation to isolate the product. Thus, this process step is avoided when using aminosilanes instead of halogen containing silanes.

Another aspect of the invention is that, because no calcination or filtration step is needed to eliminate halogen impurities, the entire reaction can, but need not, take place in one vessel and in a liquid phase. This results in greatly improved economics in the preparation of the polysilazane.

In yet another aspect of the invention, the degree of polymerization of the silazanes depends to some degree on the temperature of the reaction. Thus, it has been found that the polysilazanes produced via transamination and subsequent condensation reactions at ambient temperature will be of significantly lower molecular weight than those prepared at higher temperatures. These low molecular weight polisilizanes may be beneficial for applications requiring such low weight. Consequently, the reaction temperature can be used to impart useful properties to the polysilazanes with respect to their molecular weights depending on the desired application.

The transamination and subsequent condensation reactions can be performed efficiently in the temperature range of 20° to 200° C. in a largely unreactive solvent. Within this wide range are preferred ranges that vary based on starting reactants and the overall product morphology desired. For example, for the production of a precursor for high purity $Si_2N_4$, the reaction of $(Me_2N)_3SiH$ with $NH_3$ in the presence of a strongly acidic transamination catalyst, such as $H_2SO_4$, is preferably performed in the temperature range of 100° to 200° C. These higher temperatures result in producing a silazane polymer which is a highly crosslinked free flowing powder. This material is then ideally suited to be converted to $Si_3N_4$ powder via high temperature firing. As another example, it may be desired to prepare a silazane polymer which may be used as an impregnant in a porous pre-formed ceramic part. It would therefore be useful to prepare a silazane polymer which is a liquid which may also have the added feature of being soluble in an unreactive solvent. A likely candidate for the preparation of such a silazane polymer would be derived from the reaction of $(Me_2N)_3SiH$ with $MeNH_2$ in the presence of a mildly acidic transamination catalyst, e.g., para-toluene sulfonic acid, preferably performed in the temperature range of 20° to 80° C. As a third example it may be desired to prepare a silazane polymer which is resinous and can be formed into shapes or pulled into fibers. This silazane polymer would be required to have a significant degree of crosslinking to increase its viscosity. This necessitates performing the reaction at higher temperatures in the presence of a strong acid catalyst. For example, the reaction of a mixture of $(Me_2N)_3SiH$ and $(Me_2N)_3SiCH=CH_2$ with $MeNH_2$ in the presence of trifluoromethane sulfonic acid, preferably in the temperature range of 60° to 100° C., should afford the desired crosslinked silazane polymer.

It can be said that the transamination reaction can be effectiely performed under a variety of temperature ranges which are largely dictated by the starting reactants, the transamination catalyst, and the desired product morphology and therefore cannot be limited to any particular temperature range, in general It is also desirable, for economic reasons, for the reaction to be conducted at atmospheric pressure but any decrease or increase in pressure will demonstrate the expected effects.

Notwithstanding this use of temperature or pressure to affect the degree of polymerization, the transamination reactions of aminosilanes and alkylaminosilanes with ammonia, methylamine or other useful primary amines are not narrowly critical with regard to solvent, amount of a catalyst used, pressure, reaction equipment or temperature and may be easily put to practice without specialized equipment by those skilled in the art.

Although the starting aminosilane reactant, transaminating reactant and catalyst can generally be combined in any order, they are preferably combined in the following wày, i.e. solvent, starting aminosilane reactant, catalyst and then transaminating amine reactant. The reaction may take anywhere from 1 to 24 hours for transamination and subsequent condensation polymerization to occur.

EXAMPLES

The following specific examples and procedures are presented to illustrate the invention, but are not to be construed as limitations thereon.

| Definitions | |
|---|---|
| °C. | temperature reported in Centigrade degrees |
| gm | gram |
| mm | millimeter |
| ml | milliter |
| mol | moles |
| mmol | millimoles |
| min | minute |
| hr | hour |
| Hg | mercury |
| Me | methyl |
| GLC | Gas-Liquid Chromotography |

GENERAL PROCEDURE

All reactions were run in standard laboratory glassware of various sizes using heating mantles, magnetic stirring devices or mechanical stirring devices, thermometers and provisions for maintaining a dry nitrogen atmosphere and were run in an efficient fume hood.

All amines and aminosilanes were stored under an atmosphere of dry nitrogen. Glassware was dried at 150° C. for 1 hour before use. The exit gases from the pyrolysis was vented to a fume hood.

Laboratory pyrolyses were run in quartz reactors in a tube furnace up to 1000° C., and in alumina reactors in a tube furnace from 1000° C. to 1500° C. under dry $N_2$ purge at atmospheric pressure. Ceramic yields varied marginally by varying pyrolysis conditions for each precursor based on TGA (thermal gravimetric analysis) and DSC (differential scanning calorimetry) data.

Typical temperature profiles for the conversion of the silazane polymer product to silicon nitride in the 1000° C. and 1550° C. furnaces are shown below.
1000°C.
(1) ramp (i.e., gradually heat) from 100° to 250° C. over 2 hrs;
(2) soak (i.e., maintain) at 250C. for 4 hrs;
(3) ramp from 250° to 500° C. over 10 hrs;
(4) soak at 500° C. for 2 hrs;
(5) ramp from 500° to 1000° C. over 4 hrs;
(6) soak at 1000° C. for 4 hrs;
(7) ramp (i.e., gradually reduce heat) from 1000° to 500° C. over 4 hrs;
(8) ramp from 500° to 50° C. over 2 hrs.
1550° C.
(1) ramp from 100° to 750° C. over 30 min;
(2) soak at 750° C. for 5 hrs;
(3) ramp from 750° C. to 1200° C. over 2 hrs
(4) soak at 1200° C. for 4 hrs
(5) ramp from 1200° to 1350° C. over 4 hrs;
(6) soak at 1350° C. for 2 hrs;
(7) ramp from 1350° to 1550° C. over 6 hrs;
(8) ramp from 1550° to 200° over 6 hrs;
5° C. guaranteed soak tolerance.

ANALYSIS AND CHARACTERIZATION

In the examples below, analysis of ceramic materials was made possible primarily through the use of X-ray powder diffraction and Fourier transform Infra-red (FTIR) spectroscopy. Using X-ray powder diffraction, the diffraction lines for both alpha and beta $Si_3N_4$ were evident after high temperature firing of the ceramic precursor to 1550° C. No other crystalline phases associated with Si, $SiO_2$, $Si_2N_2O$, or $Si_2ON_2$ were detected (see powder Diffraction File, Inorganic Phases, Joint Committee on Powder Diffraction Standards, 1983). In the event that the ceramic materials were totally non-crystalline, the analyses were made by using FTIR spectroscopy where the absorption bands associated with Si—N bonding were identified (see Mazdiyasni, K.S.,Ceram. Int., 8 (1982) p. 54).

Typically, soluble ceramic precursors were characterized by conventional analytical techniques such as FTIR and $_1H$, $^{13}C$, and $^{29}Si$ NMR spectroscopy. Insoluble ceramic precursors were identified by FTIR spectroscopy (see Smith, A. L., Analysis of Silicones, Wiley, 1974).

EXAMPLE 1

Reaction of $HSi(NMe_2)_3$ with Excess $NH_3$ in the Presence of $(Me_2NH_2)+(CO_2NMe_2)$—

A 1 liter 3 neck round bottom flask with standard taper joints was fitted with a Friedrich condenser, thermometer, heating mantle, magnetic stirrer and gas sparging tube, plus valves for maintaining a dry nitrogen atmosphere coupled with a pressure release bubbler. After the addition of 200 mls of dry toluene distilled from $Na^o$ under nitrogen, the aminosilane (200 gm; 1.24 mol) was added via syringe. Ammonia was sparged through the mixture for 15 m and then the carbamate salt $(Me_2NH_2)+(CO_2NMe_2)-(16.6$ gm; 1.24 mol) was added. The reaction mixture was heated with $NH_3$ sparging and stirring to the reflux temperature 115° C. for 8 hours while monitoring the reaction via GLC for loss of starting aminosilane $HSi(NMe_2)_3$. The material inside the flask appeared to be a water white liquid during the entire length of the reaction. After 8 hours, the reaction was determined to be complete and flask was cooled and refitted with two stoppers and a by vacuum evaporation (0.1 mm Hg) and heating 80–100° C. to yield a white glassy solid. The glassy solid was washed with 100 ml of pentane and the pentane washings were discarded. The white material was transferred under $N_2$ to a 500 ml 1 neck round bottom flask and further dried under vacuum for 6 hours (0.01 mm Hg). The yield of the white free flowing glassy material was 92.9 gm. The white solid was pyrolyzed to 1000° C. under a $N_2$ purge at atmospheric pressure to give a $Si_3N_4$ composition with a yield of 65.4% based on gm material charged (5.03 gm) vs gm material obtained (3.29 gm).

EXAMPLE 2

Reaction of $HSi(NMe_2)_3$ with Excess $MeNH_2$ in Toluene and in the Presence of $(Me_2NH_2)+(CO_2NMe_2)-$ In an apparatus as described in Example 1 using a 2 liter flask instead, were combined toluene (375 ml) and $HSi(NMe_2)_3$ (369.9 gm; 2.2932 mol) via a cannulating device. The mixture was sparged with $MeNH_2$ for 15 min and then charged with the carbamate salt $(Me_2NH_2)+(CO_2NMe_2)-(30.73$ gm; 2.2932 mol). The reaction mixture was heated with $MeNH_2$ sparging and stirring to the reflux temp of 115° C. for 9 hours while monitoring the reactor via GLC for the loss of the starting aminosilane reactant during the entire length of the reaction. After 9 hours the reaction was determined to be complete and the flask was cooled and refitted with two stoppers and a vacuum adapter w/stopcock. The toluene solvent and excess methylamine were removed by vacuum evaporation to yield an off-white tacky resinous material. The resinous material was washed with 200 ml of pentane and the pentane washings were discarded. The resinous product hardened below 40° C. to give a white opaque solid. A sample of the white resin was pyrolized to 1000°C. under a $N_2$ purge at atmospheric to five a $Si_3N_4$ composition with a yield of 54.5% based on material charged (24.37 gm) vs. material obtained (13.27 gm). Changing the heating program of the furnace increased the yield to 58.5%.

EXAMPLE 3

Reaction of $HSi(NMe_2)_3$ with $3CH_2=CHCH_2NH_2$ in Toluene and in the Presence of $(Me_2NH_2)^+(CO_2NMe_2)^-$ A 1 liter 3 neck round bottom flask was fitted with a Friedrich condenser, heating mantle, magnetic stirrer, thermometer and fittings for a dry $N_2$ atmosphere and a pressure release bubbler. The apparatus was evacuated and refilled with $N_2$ before the toluene (300 ml), $HSi(NMe_2)_3$ (199.1 gm; 1.234 mol) and allyl amine (211.4 gm; 3.703 mol) were charged into the flask via a cannulating device. After stirring for 30 min without heating, the carbamate salt $(Me_2NH_2)^+(CO_2NMe_2)^-$ (16.54 gm; 1.234 mol) was added. Immediate gas evolution was observed. The reaction mixture was heated for 4 hours at a reflux temperature of 110° C. while monitoring the reaction via GLC for the starting silane $HSi(NMe_2)_3$ After 4 hours the reaction was determined to be complete and the flask was cooled and refitted with two stoppers and vacuum adapter w/stopcock. The contents of the flask appeared to be a water white liquid during the entire length of the reaction. The toluene solvent and excess allylamine were removed by vacuum evaporation (0.1 mm Hg) and heating to 80° C. The colorless liquid was pyrolyzed to 1000° C. under a $N_2$ purge at atmospheric pressure to give a $Si_3N_4$ composition with a yield of 40.0% based on material charged (5.33 gm) vs. material obtained (2.12 gm).

EXAMPLE 4

Reaction of $HSi(NMe_2)_3$ with $3C_6H_5NH_2$ in Toluene and in the Presence of $(Me_2NH_2)^+(CO_2NMe_2)^-$ An apparatus as described in Example 2 was vacuum evacuated and refilled with $N_2$ before toluene (400 ml), aniline (381.9 gm, 4.10 mol), and $HSi(NMe_2)_3$ (220.48 gm; 1.3669 mol) were charged via a cannulating device. The mixture was stirred at 20° C. for 30 min and the carbamate salt $(Me_2NH_2)^+(CO_2NMe_2)^-$(1.29 gm; $9.61 \times 10^{-3}$ mol was then added. As the reaction was brought to the reflux temperature of 117° C., vigorous gas evolution was observed. The mixture was heated at the reflux temperature for 3 hours until no further gas evolution was observed. The flask was cooled to room temperature and the contents inside the flask changed from a water white solution to a crystalline slurry. The apparatus was refitted with two glass stoppers and a vacuum adapter with stopcock. The toluene and excess aniline were removed by vacuum evaporation (0.1 mm Hg) and heating to 120° C. The resultant solid material was washed liberally with pentane, filtered and dried under vacuum to give a final yield of 328.3 gm of white crystalline needles. A sample was pyrolyzed to 1000° C. under a $N_2$ purge at atmospheric pressure to give of $Si_3N_4$ composition with a yield of 38.6% based on material charged (4.40 gm) vs. material recovered (1.70 gm).

EXAMPLE 5

Reaction of $HSi(NMe_2)_3$, with $3C_6H_5NH_2$ in Toluene and in the Presence of $(Me_2NH_2)^+(CO_2NMe_2)^-$ A 200 ml 1 neck round bottom flask was fitted with a coiled condenser, magnetic stirrer, heating mantle and fittings for maintaining a dry $N_2$ atmosphere and a pressure release bubbler. The apparatus was vacuum evacuated and refilled with $N_2$ before toluene (40 ml), aniline (27.05 gm; 0.2905 mol) and $HSi(NMe_2)_3$ (15.62 gm; 0.0968 mol) were charged via syringe. The mixture was stirred for 15 min at 20° C. before adding the carbamate salt $(Me_2NH_2)^+(CO_2NMe_2)^-$(0.129 gm, $9.61 \times 10^{-4}$ mol). As the reaction brought up to the reflux temperature of 117° C. vigorous gas evolution occurred. The mixture was heated at the reflux temp for 5 hours and a gradual decrease in gas evolution was observed. Upon completion of the reaction, determined by GLC, the work up was virtually identical as that described in Example 4, yielding 22.8 gm. of white crystalline material. A sample was pyrolyzed to 1000° C. under a $N_2$ purge at atmospheric pressure to give a $Si_3N_4$ composition with a yield of 42.4% based on material charged (7.22 gm) vs. material recovered (3.06 gm).

EXAMPLE 6

Reaction of $HSi(NMe_2)_3$ with Excess $NH_3$ in Toluene in the Presence of $CF_3SO_3H$ A 500 ml 3 neck round bottom flask was fitted with a reflux condenser, magnetic stirrer, gas sparging tube and a nitrogen adapter with a pressure release bubbler. The flask was charged with toluene (150 ml) and $HSi(NMe_2)_3$ (98.6 gm, 0.611 mol) via syringe and the water white solution was sparged with $NH_3$ for 15 minutes. After addition of $CF_3SO_3H$ (0.54 mL) via syringe the solution became cloudy. After 1 hour of $NH_3$ sparging at room temperature the contents of the flask had transformed to a white slurry. The reaction was heated for 2 hours at 50° C. and then the solvent was removed by vacuum evaporation (0.1 mm Hg) with gentle heating to give a white solid. The material was washed with pentane (200 mL) and isolated by vacuum filtration. After drying under vacuum (0.01 mm Hg) 33 6 gm of white free flowing powder was obtained. A sample of the white material was pyrolyzed via a programmed heating schedule to 1000° C. under a $N_2$ purge at atmospheric pressure to give a $Si_3N_4$ composition with a ceramic yield of 82.2% based on material charged (3.99 gm) vs material recovered (3.28 gm).

EXAMPLE 7

Reaction of $HSi(NMe_2)_3$ with Excess $CH_3NH_2$ in Toluene in the Presence of $CF_3SO_3H$ A 500 ml 3 neck round bottom flask was fitted was reflux condenser, magnetic stirrer, gas sparging tube and nitrogen adapter with a pressure release bubbler. The apparatus was charged with toluene (100 mL) and $HSi(NMe_2)_3$ (95.5 gm, 0.592 mol) via syringe and the water white liquid was sparged with for $CH_3NH_2$ 15 minutes. After the addition of $CF_3SO_3H$ (0.52 mL, 0.0059 mol) via syringe, the water white solution was sparged was $CH_3NH_2$ for an additional hour while maintaining the temperature of the reaction at 20° C. The reaction was determined to be complete after 2 hours. The solvent was removed by vacuum evaporation (0.1 mm Hg) with gentle heating to give an off-white, tacky material. Pentane (200 mL) was added and the flask was gently heated to the reflux temperature whereupon the off-white resin dissolved. The solution was allowed to cool and then filtered to give a clear filtrate. The solvent was removed yielding 46.8 gms of a white, opaque, viscous liquid. A sample of the white material was pyrolyzed via a programmed heating schedule to 1000° C. under a $N_2$ purge at atmospheric pressure to give a $Si_3N_4$ composition was a ceramic yield of 69.8% based on material charged (6.42 gm) vs material recovered (4.48 gm).

by vacuum evaporation (0.1 mm Hg) and gentle heating to 50° C. Complete removal of the solvent yielded a turbid off white semi-viscous liquid (24.0 gm). Gas chromatography/mass spectrometry identified low molecular weight products such as

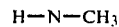

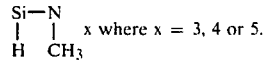

x where x = 3, 4 or 5.

TABLE I

| Example | Starting Reactant | Transaminated With | Catalyst | Mol % |
|---|---|---|---|---|
| 1 | $HSi(NMe_2)_3$ | $NH_3$ | $(Me_2NH_2)^+(CO_2NME_2)^-$ | 10 mol % |
| 2 | $HSi(NMe_2)_3$ | $MeNH_2$ | $(Me_2NH_2)^+(CO_2NMe_2)^-$ | 10 mol % |
| 3 | $HSi(NMe_2)_3$ | $CH_2=CHCH_2NH_2$ | $(Me_2NH_2)^+(CO_2NMe_2)^-$ | 10 mol % |
| 4 | $HSi(NMe_2)_3$ | $C_6H_5NH_2$ | $(Me_2NH_2)^+(CO_2NMe_2)^-$ | 10 mol % |
| 5 | $HSi(NMe_2)_3$ | $C_6H_5NH_2$ | $(Me_2NH_2)^+(CO_2NMe_2)^-$ | 1 mol % |
| 6 | $HSi(NMe_2)_3$ | $NH_3$ | $CF_3SO_3H$ | 1 mol % |
| 7 | $HSi(NMe_2)_3$ | $CH_3NH_2$ | $CF_3SO_3H$ | 1 mol % |
| 8 | $HSi(NMe_2)_3$ | $NH_3$ | $(Me_2NCO_2)(Me_2N)_2SiH$ | 10 mol % |
| 9 | $HSi(NMe_2)_3$ | $CH_3NH_2$ | $CH_3C_6H_4SO_3H.H_2O$ | 1 mol % |

Table I above is to illustrate that compounds having an Si—H aminosilane linkage are effectively catalyzed by the method of the invention by catalysts with sources of carbon dioxide (examples 1–5, 8) or by strong organic acids (examples 6, 7 and 9).

EXAMPLE 8

Reaction of $HSi(NMe_2)_3$ with Excess $NH_3$ in the Presence of $(Me_2NCO_2)(NMe_2)_2SiH$ A 250 ml three neck round bottom flask with standard taper joints fitted with a coiled condenser, magnetic stirring bar, heating mantle, magnetic stirrer and a gas sparging tube, plus valves and tubing for maintaining a dry nitrogen atmosphere coupled with a pressure release bubbler. After the addition oF 50 mls of dry toluene, the aminosilane, $HSi(NMe_2)_3$' (41.4 gm; 0.255 mol) was charged into the flask via syringe. Carbon dioxide was sparged through the solution for 5 minutes, thereby generating $(Me_2NCO_2)(Me_2)_2$ SiH in situ as set forth by examples by Hopper and Kanner in U.S. Pat. No. 4,400,526 hereby incorporated by reference. The carbon dioxide sparge was stopped and subsequently replaced by an ammonia sparge. After 1 hour at room temperature the starting aminosilane, $HSi(NMe_2)_3$' was consumed. The clear water-white liquid was allowed to stir at ambient temperature; after 2 hours the reaction mixture gelled. The reaction flask was refitted for maintaining a vacuum and the solvent was removed by vacuum evaporation (4 mmHg) for 8 hours to yield a glassy white solid (20.62 gm). The material was ground to a free flowing white powder and dried again under vacuum (0.1 mm Hg) for an additional 8 hours showing no substantial weight loss.

EXAMPLE 9

Reaction of $HSi(NMe_2)_3$ with Excess $MeNH_2$ in the Presence of $CH_3C_6H_4SO_3H.H_2O$ A reaction apparatus identical to that in Example 8 was charged with dry toluene (60 ml) and the aminosilane, $HSi(NMe_2)_3$(49.3 gm; 0.306 mol). The transamination catalyst $CH_3C_6H_4SO_3H.H_2O$ (0.582 gm; 3.06 mmol) was added as a solid. Immediate gassing was observed due to the reaction of $HSi(NMe_2)_3$ with the water of solvation of the catalyst. The reaction mixture was sparged with $MeNH_2$ at room temperature. After 1.5 hours, the aminosilane was consumed. The reaction flask was refitted so that the solvent could be removed

EXAMPLE 10

Reaction of $CH_2=CHSi(NMe_2)_3$ with Excess $NH_3$ in Toluene in the Presence of $CF_3SO_3H$ A 1 liter 3 neck round bottom flask was fitted with a reflux condenser, magnetic stirrer, gas sparging tube and a nitrogen adapter with a pressure release bubbler. The flask was charged with toluene (90 ml) and $CH_2=CHSi(NMe_2)_3$ (88.2 gm, 0.471 mol) via syringe and the water white solution was sparged with $NH_3$ for 15 minutes. After addition of $CF_3SO_3H$ (0.706 gm, 0.0047 mol) via syringe, the solution was heated to the reflux temperature (110° C.) for four hours. The reaction was determined to be complete and the solvent was removed by vacuum evaporation (0.1 mm Hg) with gentle heating yielding an off-white material (30.4 gm). A sample of the beige material was pyrolyzed to 1000° C. under a $N_2$ purge at atmospheric pressure to give a $Si_3N_4$ composition with a ceramic yield of 74.5% based on material charged (5.33 gm) vs. material recovered (3.97 gm).

EXAMPLE 11

Reaction of $CH_2=CHSi(NMe_2)_3$ with Excess $CH_3NH_2$ in Toluene in the Presence of $CF_3SO_3H$ An apparatus described in Example 8 was charged with toluene (75 ml) and $CH_2=CHSi(NMe_2)_3$ (74.2 gm, 0.396 mol) via syringe and the water white solution was sparged with $CH_3NH_2$ for 15 min. After addition of $CF_3SO_3H$ (0.59 gm, 0.00396 mol) via syringe the reaction mixture was heated to the reflux temperature (110° C.) for four hours. The reaction was determined to be complete by GLC and the toluene was removed by vacuum evaporation (0.1 mm Hg) with gentle heating (60° C.) yielding an off white waxy solid (43.5 gm). A sample of the white waxy solid was pyrolyzed at 1000° C. under a $N_2$ purge at atmospheric pressure to yield a $Si_3N_4$ composition with a ceramic yield of 34.7% based on material charged (6.26 gm) vs. material recovered (2.17 gm).

EXAMPLE 12

Reaction of Si(NMe$_2$)$_4$ with Excess NH$_3$ in the Presence of CF$_3$SO$_3$H

A 50 ml 3 neck round bottom flask was fitted with a coiled condenser, magnetic stirrer and stirring bar, gas sparging tube, thermometer and fittings for maintaining a dry nitrogen atmosphere. The flask was charged with the aminosilane, Si(NMe$_2$)$_4$, (32.8 gm, 160.78 mmol) the solvent toluene (35 ml) and the catalyst, CF$_3$SO$_3$H (0.24 gm, 1.61 mmol) via syringe. The solution was sparged with NH$_3$ for two hours at room temp and then heated to reflux approximately seven hours. Removal of the solvent by vacuum evaporation yielded a white powdery solid (18.0 gm). The white solid (4.50 gm) was fired to 1000° C., under a nitrogen atmosphere to yield a dark grey powdery solid (1.80 gm) corresponding to a ceramic yield of 40.0% based on weight charges versus weight recovered.

EXAMPLE 13

Reaction of Si(NMe$_2$)$_4$ with Excess CH$_3$NH$_2$ in the Presence of CF$_3$SO$_3$H A reaction apparatus similar to that described in Example 12 was charged with toluene (35 mls), Si(NMe$_2$)$_4$ (27.3 gm; 132.82 mmol) and CF$_3$SO$_3$H (0.20 gm; 1.3382 mmol) via syringe. The water white solution was sparged with CH$_3$NH$_2$ for 2 hours at room temperature and then heated to reflux for seven hours. Removal of the solvent by vacuum evaporation yielded a white crystalline solid (14.20 gm). The crystalline tacky solid (4.70 gm) was fired to 1000° C. under N$_2$ to yield a black crusta;;ome solid (2.85 gm) corresponding to a ceramic yield of 60.6% based on weight of material charged vs. weight material recovered.

EXAMPLE 14

Reaction of CH=CHSi(NMe$_2$)$_3$ With Excess CH$_3$NH$_2$ in the Presence of CF$_3$SO$_3$H Followed by the Addition of HSi(NMe$_2$)$_3$ and Continued CH$_3$NH$_2$ Sparging A 500 ml three neck round bottom flask was fitted with a Friedrich condenser, magnetic stirrer and stirring bar, gas sparging tube, thermometer and fittings for maintaining a dry N$_2$ atmosphere. The flask was charged with toluene (100 ml), CH$_2$=CHSi(NMe$_2$)$_3$ (48.2 gm; 0.257 mol) and CF$_3$SO$_3$H (0.39 gm; 2.57 mmol) via syringe. The solution was sparged with CH$_3$NH$_2$ for 2 hours at room temperature. The flask was then charged with HSi(NMe$_2$)$_3$ (41.5 gm; 0.257 mol) and the CH$_3$NH$_2$ was continued for another hour. After stirring overnight both of the starting aminosilanes had been consumed. The reaction mixture was heated to 110° C. for 2 hours. Subsequently the solvent was removed by vacuum evaporation to yield an off white opaque tacky resinous solid (45.5 gms). This material was soluble in pentane. It also melted at 50°-60° C. to give a pourable material which could be pulled into threads and long fibers. A portion of the off white resin (2.66 gm) was melted and poured into a quartz crucible and then fired to 1000° C. under a N$_2$ atmosphere. A solid shiny hard black piece which conformed to the shape of the quartz crucible was recovered (1.86 gm) corresponding to a ceramic yield of 69.9% based on weight material charged vs. weight material recovered.

TABLE II

| Example | Starting Reactant | Transaminated With | Catalyst | Mol % |
|---|---|---|---|---|
| 10 | CH$_2$=CHSi(NMe$_2$)$_3$ | NH$_3$ | CF$_3$SO$_3$H | 1 mol % |
| 11 | CH$_2$=CHSi(NMe$_2$)$_3$ | CH$_3$NH$_2$ | CF$_3$SO$_3$H | 1 mol % |
| 12 | Si(NMe$_2$)$_4$ | NH$_3$ | CF$_3$SO$_3$H | 1 mol % |
| 13 | Si(NMe$_2$)$_4$ | CH$_3$NH$_2$ | CF$_3$SO$_3$H | 1 mol % |

As seen from Table II, Class 2 aminosilane compounds are relatively unaffected by the mild organic acids or "CO$_2$" type catalysts which affect Class 1 compounds, and are rather more effectively transaminated using strong organic or inorganic acids.

We claim:

1. A method of preparing silazane polymers, with 3 or more repeating units, of the general formula $\pm((CH_3)_{2e}Si(R)_a(R'HN)_fH_c(NR')_g\pm$ and a (CH$_3$)$_2$NH byproduct where R is hydrogen, an alkyl group having 1-6 carbon atoms or an aryl group having 6-12 carbon atoms, a=0, or 1, =2-4, C=0-2, d=0 or 1, e=0-2, f=0-2, g=1-3 and a+c+e+f+g=4 for the polymer units; and R' is hydrogen or methyl, whereby said silazane polymer is substantially free of halide impuriites, which method comprises:

transaminating an aminosilane of the general formula (R)$_a$((CH$_3$)$_2$N)$_b$H$_c$S; where R is defined as above and a+b+c=4 with an amine of the general formula (CH$_3$)$_d$NH$_{3-d}$ whereby d is defined as above and said amine has a molecular weight lower than 45 all in the presence of an acid catalyst or the ammonium salt of said acid and thereafter condensing to form the polymer.

2. The method of claim 1 wherein c=1 or 2.

3. The method of claim 1 wherein a=o, b=3, c=1, and d=o.

4. The method of claim 1 wherein a=o, b=3, c=1, and d=1.

5. The method of claim 1 wherein R equals CH=CH$_2$, a=1, b=3, c=o, and d=o.

6. The method of claim 1 wherein R equals CH=CH$_2$, a=1, b=3, c=o and d=1.

7. The method of claim 1 wherein R equals methyl or ethyl, a=1, b=3, c=o, and d=o.

8. The method of claim 1 wherein R equals methyl or ethyl, a=1, b=3, c=o, and d=1.

9. The method of claim 1 wherein the catalyst is a strong organic or inorganic acid having a pKa of less than 2.2 or the ammonium salt of said catalyst.

10. The method of claim 9 wherein said strong organic or inorganic acid is selected from the group consisting of trifluoromethylsulfonic acid, para-toluene sulfonic acid, methylsulfonic acid, sulfuric acid, nitric acid, phosphoric acid, and trifluoroacetic acid.

11. The method of claim 2 wherein the catalyst is a source of carbon dioxide.

12. The method of claim 11 wherein the catalyst is selected from the group consisting of carbon dioxide, ammonium carbamate salts, and carbamatosilane.

13. The method of claim 1 wherein the transaminating reaction is run at a temperature of 20°-200° C.

14. The method of claim 13 wherein the temperature at which the transaminating reaction is run and the transamination catalyst vary depending on the overall morphology desired on the final silicone nitride product.

15. The method of claim 14 wherein, in the production of high purity silicone nitride, the transaminating reaction is run at a temperature of 100°–200° C. in the presence of a strongly acid catalyst.

16. The method of claim 15 wherein the strongly acidic catalyst is $H_2SO_4$.

17. The method of claim 14 wherein, in the production of silazane polymers to be used as impregnants in porous preformed ceramic parts, the transaminating reaction is run at a temperature of 20°–80° C. in the presence of a mildly acidic catalyst.

18. The method of claim 17 wherein the mildly acidic catalyst is para-toluene sulfonic acid.

19. The method of claim 1 wherein the transaminating reaction is run in a solvent which is largely unreactive under the reaction conditions.

20. The method of claim 19 wherein said solvent is selected from the group consisting of alkanes and alkylated benzenes having 6–20 carbon atoms wherein the reaction products are insoluble.

21. The method of claim 19 wherein the solvent is selected from the group consisting of alkanes and alkylated benzenes having 6–10 carbon atoms wherein the reaction products are soluble.

22. The method of claim 19 wherein the solvent is toluene or xylene.

23. The method of claim 1 wherein the starting aminosilane reactant comprises a mixture of polymers as defined by the aminosilane general formula transaminated with amine.

24. The method of claim 23 wherein the starting aminosilane reactants are mixtures of tris(dimethylamino)silane and vinyltris(dimethyamino) silane transaminated with $NH_3$ 25. The method of claim 23 wherein the starting aminosilane reactants are mixtures of tris(dimethylamino)silane and vinyl-tris(dimethylamino)silane transmitted with $CH_3 NH_2$ 26. The silazane polymers produced by the method of claim 1.

27. The silazane polymers produced by the method of claim 1 wherein c=1 or 2.

28. The silazane polymers produced by the method of claim 14.

29. The silazane polymers produced by the method of claim 1 wherein the starting reactant comprises a mixture of polymers as defined by the aminosilane general formula transaminated with amine.

30. The silazane polymers produced by the method of claim 1 wherein the starting aminosilane reactants are mixtures of tris(dimethylamino)silane and vinyl-tri(-dimethylamino)silane transaminated with $NH_3$.

31. The silazane polymers produced by the method of claim 1 wherein the starting aminosilane reactants are mixtures of tris-(dimethylamino)silane and vinyl-tris(-dimethylamino)silane transaminated with $CH_3NH_2$.

32. The silicon nitride-containing ceramics prepared from the silazane polymers of claim 26.

33. The silicon nitride-containing ceramics prepared from the silazane polymers of claim 27.

34. The silicone nitride-containing ceramics prepared from the silazane polymers of claim 28.

35. The silicon nitride-containing ceramics prepared from the silazane polymers of claim 29.

36. The silicon nitride-containing ceramics prepared from the silazane polymers of claim 30.

37. The silicon nitride-containing ceramics prepared from the silazane polymers of claim 31.

* * * * *

UNITED STATES PATENT AND TRADEMARK OFFICE
CERTIFICATE OF CORRECTION

PATENT NO. : 4,675,424

DATED : June 23, 1987

INVENTOR(S) : Roswell E. King, III, Bernard Kanner, Steven P. Hopper, Curtis L. Schilling, Jr.

It is certified that error appears in the above-identified patent and that said Letters Patent is hereby corrected as shown below: Title page:

Seventh line from the bottom of the Abstract: "$(R)_a((CH_3)_2N)_bH_cS$" should read --- $(R)_a((CH_3)_2N)_bH_cSi$ ---.

Column 1, line 26: "N2" should read --- $N_2$ ---.

Column 3, line 36: "6-2" should read --- 6-12 ---.

Column 4, line 15: Insert a comma after "diamine".

Column 4, line 67: "$(R_{22})$" should read --- $(R_2NCO_2)$ ---.

Column 5, line 33: "amlnosilane" should read --- aminosilane ---.

Column 6, line 14: "$Si_2N_4$" should read --- $Si_3N_4$ ---.

Column 6, line 46: "effectiely" should read --- effectively ---.

Column 8, line 15: "$_1H$" should read --- $^1H$ ---.

Column 8, line 22: "$(Me_2NH_2)+(CO_2NMe_2)$" should read --- $(Me_2NH_2)^+(CO_2NMe_2)^-$ ---.

Column 8, line 41: replace the article "a" with the phrase: --- the toluene solvent and excess ammonia were removed ---.

Column 9, line 11: "five" should read --- give ---.

Column 9, line 54: Insert the closing parenthesis sign --- ) --- after the word "mol".

UNITED STATES PATENT AND TRADEMARK OFFICE
CERTIFICATE OF CORRECTION

PATENT NO. : 4,675,424

DATED : June 23, 1987

INVENTOR(S) : Roswell E. King, III, Bernard Karner, Steven P. Hopper, Curtis L. Schilling, Jr.

It is certified that error appears in the above-identified patent and that said Letters Patent is hereby corrected as shown below:

Column 10, line 47: "336" should read --- 33.6 ---.

Column 10, line 63: "for $CH_3NH_2$" should read --- $CH_3NH_2$ for ---.

Column 10, line 66: "was" should read --- with ---.

Column 10, line 11: "was" should read --- with ---.

Column 11, lines 57 and 62, the formula should read:
--- $CH_3C_6H_4SO_3H \cdot H_2O$ ---.

Column 12, lines 6 to 12, the formula should read:

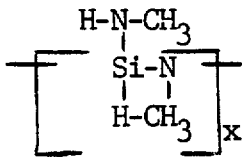

Column 13, line 21: "charges" should read --- charged ---.

Column 13, line 36: "crusta;;ome" should read --- crystalline ---.

Column 14, lines 20-21: the formula should read:
--- $\{((CH_3)_2N)_e Si(R)_a (R'NH)_f H_c (NR')_g\}$ ---.

Column 14, line 24: "= 2-4" should read --- b = 2-4 ---.

Column 14, line 30, the formula should read: --- $(R)_a ((CH_3)_2N)_b H_c Si$ ---.

Signed and Sealed this

Twenty-fourth Day of January, 1989

Attest:

DONALD J. QUIGG

Attesting Officer

Commissioner of Patents and Trademarks